(12) United States Patent
Proksa

(10) Patent No.: US 6,879,655 B2
(45) Date of Patent: Apr. 12, 2005

(54) COMPUTED TOMOGRAPHY APPARATUS

(75) Inventor: Roland Proksa, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 202 days.

(21) Appl. No.: 10/325,467

(22) Filed: Dec. 20, 2002

(65) Prior Publication Data

US 2003/0142778 A1 Jul. 31, 2003

(30) Foreign Application Priority Data

Dec. 20, 2001 (DE) .......................... 101 62 768

(51) Int. Cl.[7] .............................................. A61B 6/00
(52) U.S. Cl. ............................... 378/4; 378/8; 600/425; 600/428
(58) Field of Search .......................... 378/4, 8, 15, 19, 378/901; 600/425, 428

(56) References Cited

U.S. PATENT DOCUMENTS 5,430,783 A * 7/1995 Hu et al. ........................ 378/15
6,269,141 B1 * 7/2001 Proksa et al. ................. 378/19

FOREIGN PATENT DOCUMENTS

EP 0 981 995 A2 7/1999

OTHER PUBLICATIONS

R. Prosksa, et al.; "The n–PI–Method for Helial Cone–Beam CT"; IEEE Transactions on Medical Imaging, vol. 19, No. 9, Sept. 2000, pp. 848–863.

* cited by examiner

Primary Examiner—Edward J. Glick
Assistant Examiner—Courtney Thomas
(74) Attorney, Agent, or Firm—Thomas M. Lundin

(57) ABSTRACT

The invention relates to a computed tomography apparatus in which measuring data of a patient is acquired along a helical trajectory by means of a conical radiation beam. The size of the detector window is then a factor of 3, 5, 7 . . . larger than the distance between neighboring turns of the helix. In order to select from among the acquired redundant data the data which is suitable for completely filling the Radon domain so as to achieve exact reconstruction, in accordance with the invention it is proposed to provide a cardiac motion signal detection device for the detection of a cardiac motion signal representing the cardiac motion and to arrange the reconstruction unit so as to select such measuring data from among the measuring data regionally redundantly filling the Radon domain that the Radon domain is completely and homogeneously filled with measuring data from cardiac motion phases with as little motion as possible.

8 Claims, 3 Drawing Sheets

COMPUTED TOMOGRAPHY APPARATUS

BACKGROUND

Figure 1:
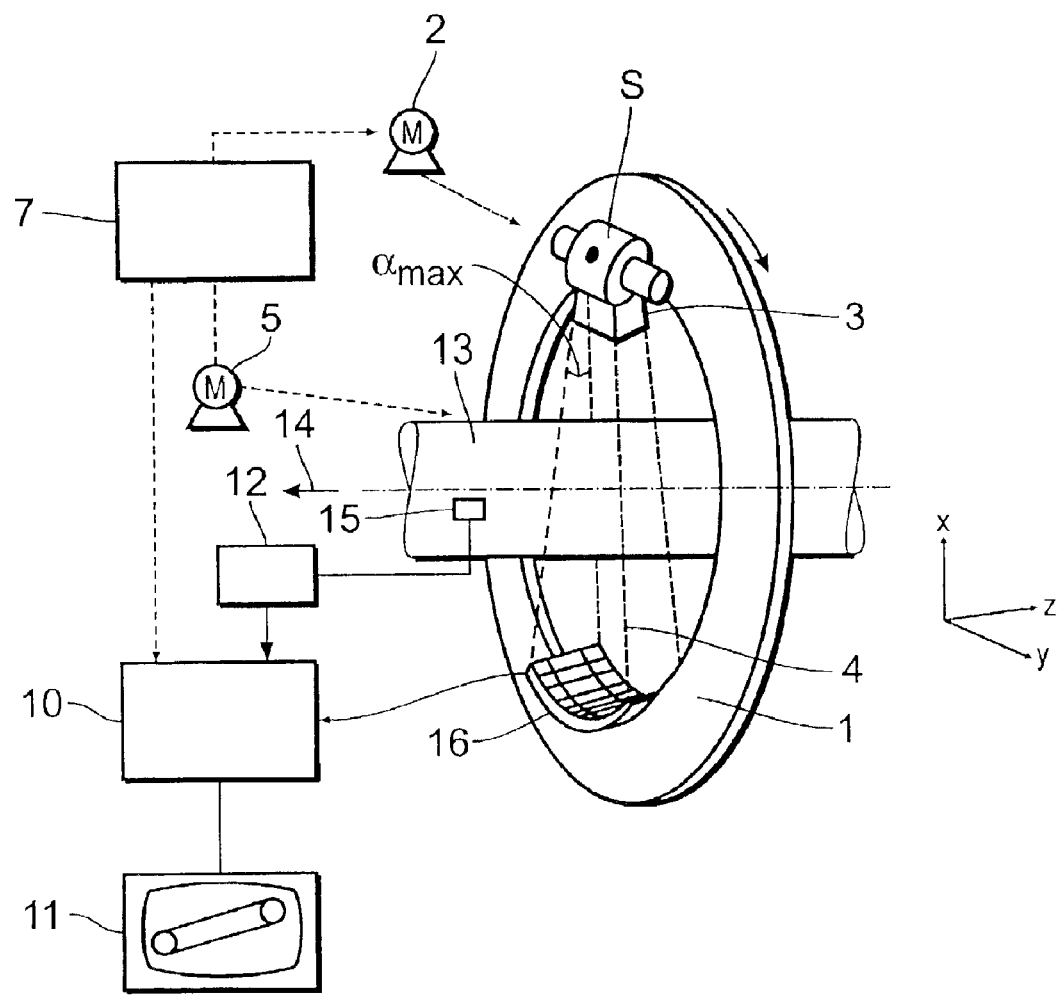

The invention relates to a computed tomography apparatus which includes a scanning unit with a radiation source and a detector unit which is connected thereto in order to detect a conical radiation beam, emitted by the radiation source, after its passage through the examination zone of a patient who is situated between the radiation source and the detector unit,
a drive unit for producing a relative motion, formed as a helix around an axis of rotation, between the scanning unit and the patient, and
a reconstruction unit for reconstructing a 3D image data set of the examination zone from the measuring data acquired by the detector unit within a detector window defined by the helix, the connecting lines from the radiation source to the two edges of the detector window, being offset relative to one another in the direction of the axis of rotation, intersecting two segments of the helix which are offset by the distance (2n+1)p in the direction of the axis of rotation, where n is a small integer number larger than or equal to 1 and p corresponds to the axial offset between two neighboring turns of the helix, so that the Radon domain is regionally filled with a different degree of redundancy by the measuring data.

A computed tomography apparatus of this kind (also referred to hereinafter as CT apparatus) is known from EP 0 981 995 A2. The scanning trajectory in this computed tomography apparatus is shaped as a helix and a conical radiation beam traverses the examination zone of an object to be examined, for example, a patient. In the cited publication it is also proposed to choose the dimensions of the detector window (or the part thereof which is used for the reconstruction) so as to be a factor of 3, 5, 7 . . . larger than the distance between neighboring turns of the helix. When such a geometry is chosen, each voxel in the examination zone is irradiated exactly from an angular range of $3\pi$, $5\pi$, $7\pi$, . . . when it passes through the radiation cone. Consequently, the Radon domain is filled at least regionally with a multiple redundancy of, for example, 3, 5, 7 times. Such a data acquisition ultimately enables an enhanced image quality to be achieved.

The use of computed tomography for imaging in the cardiac region often gives rise to images containing artifacts which are due to the cardiac motion during the data acquisition. In order to reduce such artifacts, use is often made of reconstruction methods in which a cardiac motion signal, for example, an ECG signal, which has been additionally acquired during the acquisition of the measuring data is evaluated in order to base the reconstruction exclusively on the measuring data which has been acquired during cardiac phases with little motion. However, it must be ensured that an adequate number of data from such cardiac motion phases with little motion of the heart is indeed available for the reconstruction as otherwise reconstruction of a 3D image data set cannot be performed at all.

A further problem is encountered in that the examination zone of interest of a patient is larger than the volume which can be scanned by way of a circular trajectory. Therefore, helical trajectories are often used for the acquisition of the measuring data; in that case it is necessary to acquire measuring data with a degree of redundancy so as to enable the described reconstruction with evaluation of the cardiac motion signal (so-called gated reconstruction) to be carried out.

SUMMARY

It is an object of the invention to provide a further improvement of the computed tomography apparatus of the kind set forth and to enable notably exact reconstruction.

This object is achieved in that there is provided a cardiac motion signal detection device for the detection of a cardiac motion signal representing the cardiac motion, and in that the reconstruction unit is arranged to select, on the basis of the cardiac motion signal, such measuring data from among the measuring data regionally redundantly filling the Radon domain that the Radon domain is completely and homogeneously filled with measuring data from cardiac motion phases with as little motion as possible.

The invention is based on the recognition of the fact that suitable data can be selected from the redundant data on the basis of the cardiac motion signal detected during the acquisition of the measuring data, so that the Radon space can be homogeneously and completely filled and as non-redundant as possible, thus enabling exact reconstruction of a 3D data set. Measuring data acquired from cardiac motion phases with as little motion as possible, for example, briefly before the occurrence of the R deflection in an ECG, is advantageously selected. The reconstruction can then take place, for example, by means of the reconstruction method disclosed in "The n-PI-Method for Helical Cone Beam CT", R. Proksa, T. Köhler, M. Grass, J. Timmer, IEEE Transactions and Medical Imaging, Vol. 19, no. 9, 2000.

Advantageous embodiments of the computed tomography apparatus are disclosed herein. In conformity with a preferred embodiment the parameter n preferably as the value 1 or 2, the distance between the edges of the detector window amounts to three times or five times the distance between two turns of the helix. Like in the known computed tomography apparatus, the detector window can be realized by appropriately shaping the detector unit and/or the conical radiation beam formed by a collimator of the radiation source.

Preferably, an electrocardiograph is used as the cardiac motion signal detection unit for measuring an electrocardiogram during the measuring data acquisition. Alternatively, the cardiac motion signal can also be determined directly from the measuring data acquired. For example, it is known that the center of gravity of an acquired measuring data distribution, or an image, is preserved in the reconstructed projection data. The position in space of the center of gravity, however, generally changes as a function of the motion of the anatomy, for example, in conformity with the cardiac motion. This aspect can be advantageously used to derive a cardiac motion signal from changes of the position of the center of gravity of various projection data or images.

In the computed tomography apparatus in accordance with the invention not all regions of the Radon domain are filled with an equally high redundancy. All Radon planes having a region-related number of intersections with the helical trajectory of the radiation source are situated in each region. In other words, all Radon planes having a single intersection with the helix are situated in one region and all Radon planes having three intersections with the helix are situated in another region, etc. Different categories of regions can thus be distinguished. Therefore, in a preferred embodiment it is arranged that in regions with a single or multiple redundancy, after selection of measuring data which is suitable with a view to little cardiac motion, the suitable measuring data is averaged so as to fill this region of the Radon domain with a reduced redundancy. On the other hand, should the selection with a view to little motion reveal that regionally no measuring data at all can be used to fill the Radon domain in the relevant region, interpolation from neighboring measuring data can also be carried out.

In accordance with a further embodiment of the invention the measuring data used for filling the Radon domain is selected in such a manner that the redundant regions of the Radon domain are subdivided into sub-regions, preferably into n sub-regions, and that on the basis of the cardiac motion signal sub-regions are selected whose associated measuring data completely and homogeneously fills the Radon space from cardiac motion phases with as little motion as possible. The Radon domain is preferably subdivided into triangular regions which themselves are subdivided into individual regions again. Each of these sub-regions is associated with segments of the detector window which are formed by the helical trajectory. The triangular regions are thus subdivided into smaller triangles again, that is, preferably in n triangles. Because sub-regions overlap in redundant regions of the Radon domain, resulting in said redundancy, in conformity with this embodiment the sub-regions are selected on the basis of the cardiac motion signal in such a manner that ultimately the Radon domain is again completely and homogeneously filled. In the case of triangular sub-regions the Radon domain is thus completely filled with suitable triangular sub-regions.

In a further preferred embodiment it may be arranged that the measuring data is weighted upon the averaging of a plurality of measuring data, the weighting being dependent on the strength of the cardiac motion detected during the acquisition of the individual measuring data. Consequently, this means that measuring data acquired in the presence of less cardiac motion are weighted more during averaging than measuring data originating from a cardiac motion phase with stronger cardiac motion. Ultimately, this again results in an improved reconstruction and an enhanced image quality.

The invention also relates to a computed tomography method which includes the steps of: detecting a conical radiation beam, emitted by the radiation source, after its passage through the examination zone of a patient, situated between the radiation source and the detector unit, while utilizing a scanning unit with a radiation source and a detector unit which is connected thereto, producing a relative motion, formed as a helix around an axis of rotation, between the scanning unit and the patient by means of a drive unit, and reconstructing a 3D image data set of the examination zone from the measuring data acquired by the detector unit within a detector window, defined by the helix, by means of a reconstruction unit, the connecting lines from the radiation source to the two edges of the detector window, being mutually offset in the direction of the axis of rotation, intersecting two segments of the helix which are offset by the distance (2n+1)p in the direction of the axis of rotation, where n is a small integer number larger than or equal to 1 and p corresponds to the axial offset between two neighboring turns of the helix, so that the Radon domain is regionally filled with a different degree of redundancy by the measuring data, characterized in that a cardiac motion signal representing the cardiac motion is detected by means of a cardiac motion signal detection device, and that on the basis of the cardiac motion signal such measuring data is selected from among the measuring data regionally redundantly filling the Radon domain that the Radon domain is completely and homogeneously filled with measuring data from cardiac motion phases with as little motion as possible. This method may be further elaborated in the same or similar way as the described computed tomography apparatus in accordance with the invention.

DRAWINGS

Figure 2:
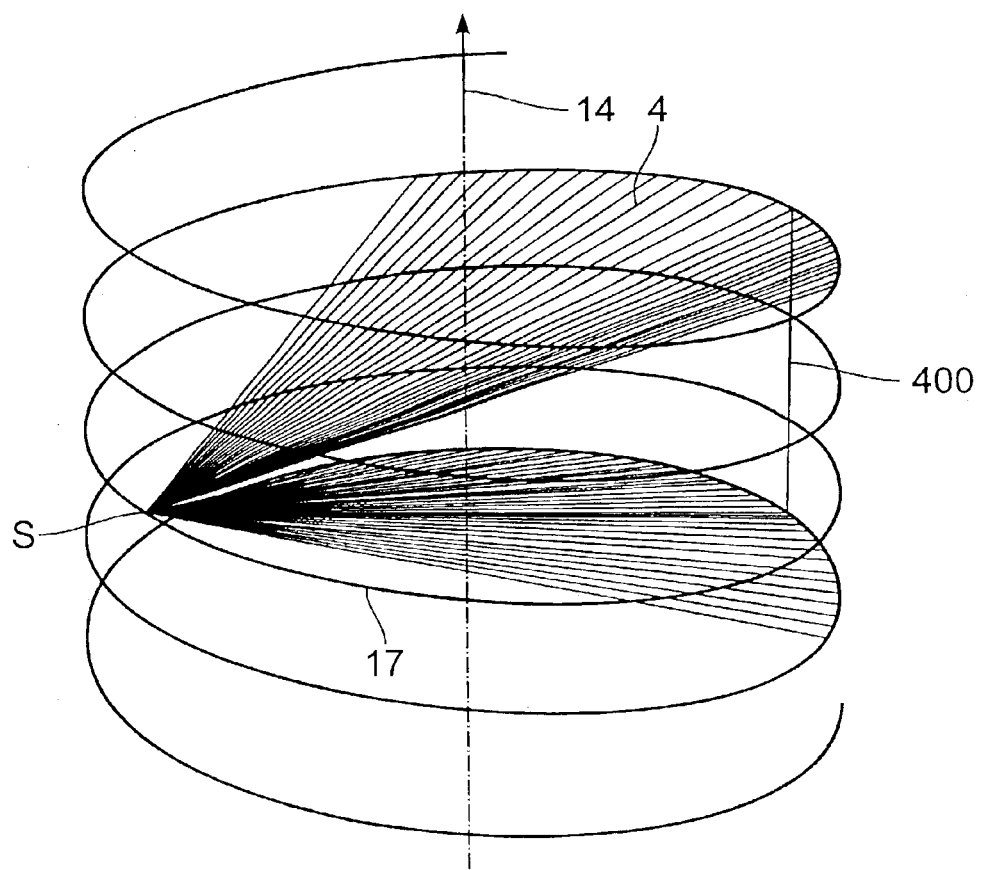
Figure 3:
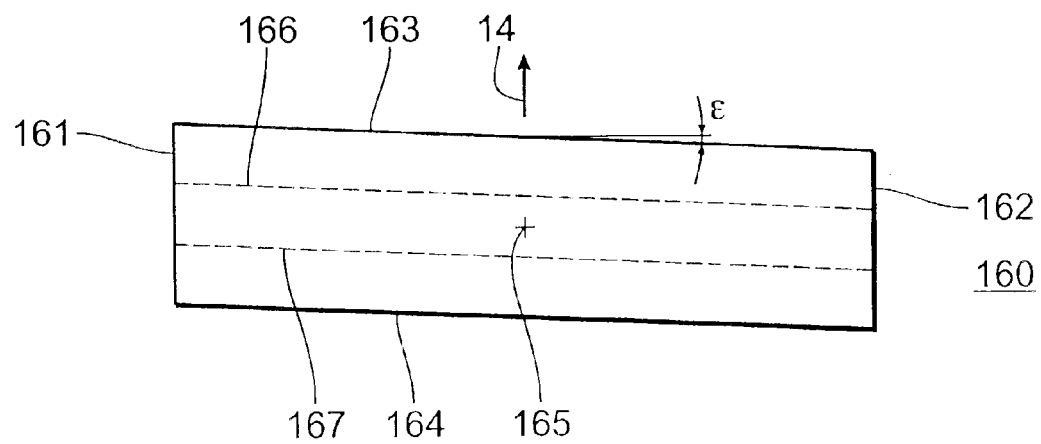
Figure 4:
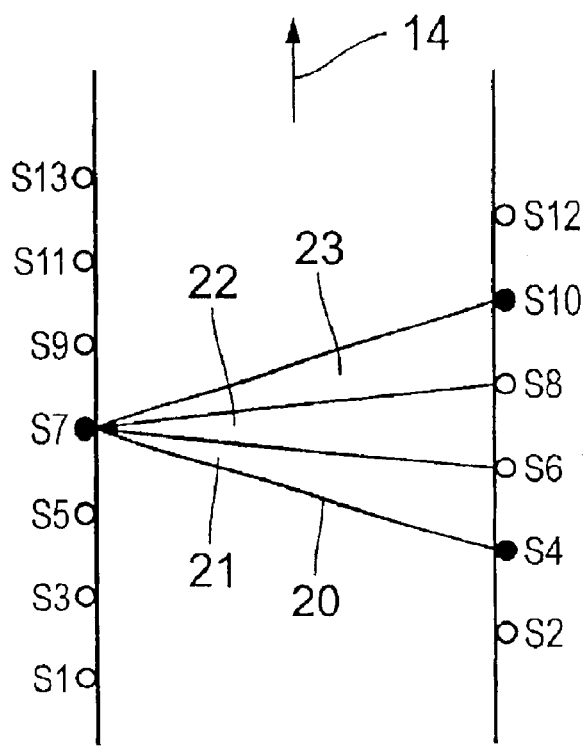
Figure 5:
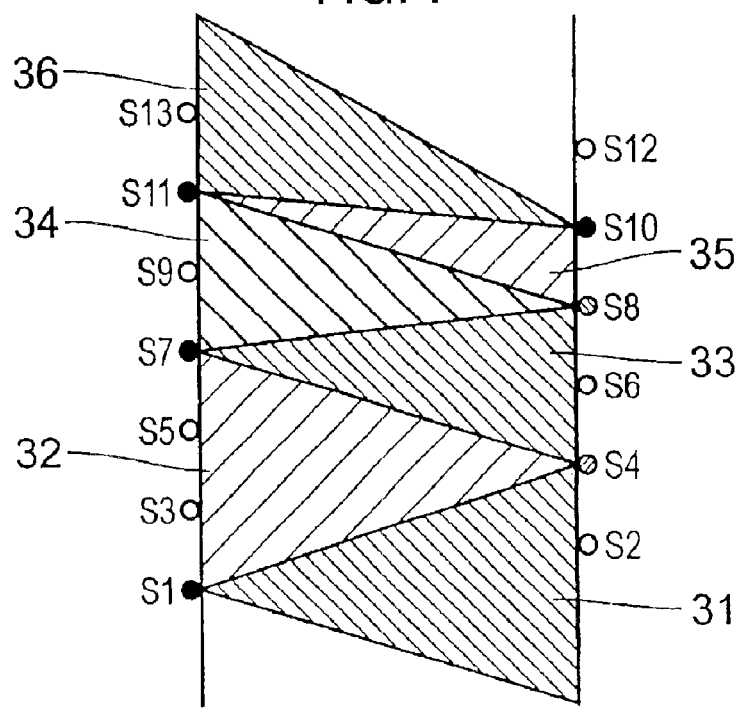

The invention will be described in detail hereinafter with reference to the drawings. Therein:

FIG. 1 is a diagrammatic representation of a computed tomography apparatus in accordance with the invention, FIG. 2 shows a configuration of a helical scanning trajectory, FIG. 3 shows a development of a detector unit, FIG. 4 shows a Radon plane of the Radon domain with a number of radiation source positions, and FIG. 5 shows a Radon plane with several sub-regions.

DESCRIPTION

The computed tomography apparatus shown in FIG. 1 includes a gantry 1 which is capable of rotation about an axis of rotation 14 which extends parallel to the z direction. To this end, the gantry is driven at a preferably constant but adjustable angular speed by a motor 2. A radiation source S, for example, an X-ray tube, is mounted on the gantry 1. The X-ray source is provided with a collimator device 3 which forms a conical radiation beam 4 from the radiation produced by the X-ray source S. The radiation beam 4 traverses a patient (not shown) who is present in a cylindrical examination zone 13. After having traversed the examination zone 13, the X-ray beam 4 is incident on a two-dimensional detector unit 16 which is mounted on the gantry 1.

The angle of aperture $\alpha_{max}$ of the radiation beam 4 (the angle of aperture is defined as the angle enclosed by a ray of the beam 4 which is situated at the edge in the x–y plane relative to a plane defined by the radiation source S and the axis of rotation 14) then determines the diameter of the examination zone 13 within which the object to be examined must be present during the acquisition of the measuring values. For example, the patient who is arranged on a patient table in the examination zone 13 can then be displaced parallel to the direction of the axis of rotation 14, or the z axis, by means of a motor 5.

The measuring data acquired by the detector unit 16 is applied to a reconstruction unit 10 which reconstructs therefrom the absorption distribution in the part of the examination zone 13 which is irradiated by the radiation cone 4 in order to display it, for example, on a monitor 11. The two motors 2 and 5, the reconstruction unit 10, the radiation source S and the transfer of the measuring data from the detector unit 16 to the reconstruction unit 10 are controlled by a suitable control unit 7.

The motors 2 and 5 can be controlled in such a manner that the ratio of the speed of advancement of the examination zone 13 to the angular velocity of the gantry 1 is constant, so that the radiation source S and the examination zone 13 move relative to one another along a helical path which is the so-called trajectory. It is in principle irrelevant whether the scanning unit consisting of the radiation source S and the detector unit 16 or the examination zone 13 performs the rotary motion or the advancing motion; only the relative motion is of importance.

In the embodiment of the invention as shown a cardiac motion signal is detected, simultaneously with the acquisition of the measuring data, by means of an electrocardiograph 12 and a sensor 15 provided on a patient. This signal is also applied to the reconstruction unit 10 in order to carry out the selection of the measuring data suitable for the reconstruction in such a manner that only measuring data acquired in low-motion cardiac motion phases are used. It is to be noted again that the cardiac motion signal can also be derived in a manner other than by means of an ECG; for example, it can be derived directly or indirectly from the measuring data acquired by the scanning unit.

FIG. 2 shows a helical trajectory 17 along which the radiation source S and the detector unit 16 (not shown) move around the examination zone 13 (not shown). The conical radiation beam emitted by the radiation source S may be considered to be composed of a plurality of fan-shaped beams which are situated in planes which extend parallel to the axis of rotation 14 and intersect one another in the radiation source S. Even though this radiation beam also contains rays which are grouped in a fan-shaped manner in other planes, hereinafter only combinations of rays which are situated in a plane parallel to the axis of rotation 14, like the fan-shaped beam 400, will be referred to as fan-shaped beams. The angle of aperture $\alpha_{max}$ of the radiation beam 4 is proportioned so that its outer fan-shaped beams are exactly tangent to the examination zone. If $\alpha_{max}=30°$, the radius of the examination zone 13 amounts to exactly half the radius of the helical trajectory. The aperture of the collimator arrangement 3 is shaped so that two turns of the helix 17 which face the radiation source and are offset by the distance 3p relative to one another (p corresponds to the advance in the z direction during one complete revolution of the radiation source S) are coincident with the rays at the upper edge and the lower edge of the radiation beam 4.

The upper edge and the lower edge of the detector window are coincident with the projection of the turns of the helix 17, or with the segments thereof which face the radiation source, on the detector unit; this means that the connecting lines from the radiation source to said edges intersect said turns.

FIG. 3 shows the development of the detector window 160 from the cylinder defined by the helix 17 into the plane of drawing. The development has the shape of a parallelogram having sides 161, 162 extending parallel to the z direction, the distance between said sides being larger as the angle of aperture $\alpha_{max}$ of the radiation beam is larger. For the length of the sides, that is, for the height h of the detector window, it holds that h=3p. The upper edge 163 and the lower edge 164 of the detector window 160 enclose an angle $\epsilon$ relative to the perpendicular to the axis of rotation 14, which angle can be calculated in conformity with the relation tan $\epsilon=p/2\pi R$, is where R is the distance between the radiation source and the axis of rotation. In this respect it is assumed that the speed of advancement and the rotary speed are constant. FIG. 3 also shows the center 165 of the detector window 160; the dashed lines 166 and 167 represent the projection of the two turns which are situated between the turns of the helix 17 which coincide with the upper edge 163 and the lower edge 164, respectively.

Each point in the examination zone is projected onto the lower edge 164 upon entering the conical radiation beam 4 and onto the upper edge 163 upon leaving the radiation beam 4. It can be demonstrated that the radiation source S performs a rotation of exactly $3\pi$ around the relevant point while its projection travels from the lower edge 164 to the upper edge 163. In relation to the axis of rotation 14, however, the rotary motion performed by the radiation source S may also be larger or smaller than $3\pi$. For further details of this n-PI method reference is made to the previously cited EP 0 981 995 A2 whose description is assumed to be incorporated in the present application.

The described computed tomography apparatus is suitable for carrying out the n-PI method in which individual regions of the Radon domain are filled with a different degree of redundancy by means of the acquired measuring data, that is, in dependence on the choice of n. In the present example n=3, so that individual regions have a triple redundancy. According to the n-PI method the Radon planes of the Radon domain are subdivided into triangular regions. FIG. 4 shows a single Radon plane with such a triangular region 20. The helical trajectory is shown in the form of a cross-sectional lateral view, so that the points of intersection of the Radon plane and the trajectory are indicated in the positions S1 to S13 for a $3\pi$ scan. The triangular region 20 which is irradiated by the radiation source in the position S7 is shown by way of example. As is demonstrated in the cited article by R. Proksa et al., the combination of all triangular regions irradiated from the individual radiation source positions cover the Radon plane shown exactly three times.

Generally speaking, the n-PI method requires the calculation of the first radial derivative of the Radon domain. These values can be calculated from diverging 2D fan beam projection segments which intersect the Radon plane. Hereinafter it will be explained how quasi-complete and homogeneous, as much as possible non-redundant regions of all Radon planes are obtained. Depending on the degree of redundancy, however, it may occur that not all necessary Radon values can be calculated from the acquired measuring data. However, it is assumed that the Radon domain is filled with a density which is adequate to enable simple interpolation of missing Radon values.

It is assumed that measuring data has first been acquired by means of the n-PI method as described above. The Radon domain is subdivided into regions. Radon planes having a region-related number of points of intersection with the helical trajectory of the radiation source are all present in each region. In other words, all Radon planes having one point of intersection with the helix lie in a first region, while all Radon planes having three points of intersection are situated in a second region, etc. The number of points of intersection is denoted by the reference m. In that case three different categories of regions can be distinguished.

a) The region with m=1: these Radon planes are irradiated only once. When the cardiac motion signal enables the use of the acquired data, that is, when the acquisition of this measuring data took place in a cardiac motion phase with sufficiently little cardiac motion, this measuring data is used. Otherwise the missing Radon values must be interpolated from neighboring values.

b) The regions with 1<m≦n: this Radon plane is fully irradiated by all m radiation source positions. First it is established which measuring data can be used from which radiation source positions in conformity with the cardiac motion signal. If no radiation sources can be used, the missing Radon values are interpolated from neighboring values. When measuring data from one or more radiation source positions can be used, the measuring data is advantageously averaged.

c) The regions with m≧n: in these regions first a finer segmentation of the measuring data is performed. Each triangular region is further subdivided into n individual sub-regions. FIG. 4 also shows such sub-regions 21, 22, 23 of the triangular region 20. With each of these sub-regions there are associated segments of the detector which are formed by the subdivision of the detector by way of the helical trajectory. In other words, the detector is subdivided into an inner PI window, the upper part and the lower part relative to the 3-PI window, etc., until ultimately n sub-regions are formed. On the basis of the subdivision the suitable measuring data is selected and feasible combinations of the sub-regions are searched so that the Radon plane is completely and homogeneously filled. If no feasible combinations are found again, missing Radon values are interpolated. In the case of measuring data which can be used several times, averaging can be performed again.

FIG. 5 shows a Radon plane which is covered completely by a suitable combination of triangular sub-regions 31 to 36. The data for filling these sub-regions 31 to 36 originate from measuring data acquired in radiation source positions S1, S4, S7, S8, S10 and S11. As can be readily seen, not all measuring data acquired in each radiation source position are used; for example, from among the measuring data acquired in the radiation source position S11 only the measuring data which is situated in the sub-region 35 is used to fill the Radon plane.

The method of selecting the measuring data can be modified in such a manner that the radiation source positions or measuring data which can be used are given different priorities on the basis of an estimate as to how near they are situated to the cardiac phase, that is, how strong the cardiac motion was during the acquisition of the corresponding measuring data. The stronger the cardiac motion was, the less the measuring data can be weighted, that is, in as far as a combination of the measuring data is performed so as to fill the Radon plane.

The computed tomography apparatus and the method in accordance with the invention enable completely filling of the Radon domain so as to obtain an exact reconstruction of a 3D data set. In accordance with the invention measuring data is selected from cardiac motion phases with as little motion as possible in order to achieve an as high as possible image quality. The reconstruction itself can then be performed by means of known methods. A reconstruction method of this kind is disclosed in the cited EP 0 981 995 A2 as well as in the cited article by R. Proksa et al. which is explicitly incorporated herein by way of reference.

What is claimed is:

1. A computed tomography apparatus which includes a scanning unit with a radiation source and a detector unit connected thereto to detect a conical radiation beam, emitted by the radiation source, after its passage through an examination zone of a patient situated between the radiation source and the detector unit,
    a drive unit for producing a relative motion, formed as a helix around an axis of rotation, between the scanning unit and the patient, and
    a reconstruction unit for reconstructing a 3D image data set of the examination zone from measuring data acquired by the detector unit within a detector window defined by the helix, the connecting lines from the radiation source to the two edges of the detector window, being offset relative to one another in the direction of the axis of rotation, intersecting two segments of the helix which are offset by a distance $(2n+1)p$ in the direction of the axis of rotation, where n is a small integer number larger than or equal to 1 and p corresponds to an axial offset between two neighboring turns of the helix, so that the Radon domain is regionally filled with a different degree of redundancy by the measuring data,
    and a cardiac motion signal detection device for the detection of a cardiac motion signal representing the cardiac motion, wherein the reconstruction unit is arranged to select, on the basis of the cardiac motion signal, such measuring data from among the measuring data regionally redundantly filling the Radon domain; the Radon domain being completely and homogeneously filled with measuring data from cardiac motion phases with as little motion as possible.

2. A computed tomography apparatus as claimed in claim 1, wherein n equals 1 or 2.

3. A computed tomography apparatus as claimed in claim 1, wherein the cardiac motion signal detection device is an electrocardiograph.

4. A computed tomography apparatus as claimed in claim 1, wherein the cardiac motion signal detection device includes means for deriving the cardiac motion signal from the measuring data acquired.

5. A computed tomography apparatus as claimed in claim 1, wherein the measuring data used for filling the Radon domain is selected in such a manner that averaging is performed when a plurality of measuring data can be used while interpolation of neighboring measuring data takes place if no usable measuring data is available.

6. A computed tomography apparatus as claimed in claim 1, wherein the measuring data for filling the Radon domain is selected in such a manner that the redundant regions of the Radon domain are subdivided into sub-regions, preferably in n sub-regions, and that on the basis of the cardiac motion signal sub-regions are selected whose associated measuring data fills the Radon domain fully and homogeneously from cardiac motion phases with as little motion as possible.

7. A computed tomography apparatus as claimed in claim 1, wherein weighting of the measuring data is performed upon the averaging of a plurality of measuring data, the weighting being dependent on the strength of the cardiac motion detected during the acquisition of the individual measuring data.

8. A computed tomography method which includes the steps of:
    detecting a conical radiation beam, emitted by a radiation source, after its passage through an examination zone of a patient, situated between the radiation source and a detector unit,
    producing a relative motion, formed as a helix around an axis of rotation, between the radiation source and the patient by means of a drive unit, and
    reconstructing a 3D image data set of the examination zone from measuring data acquired by the detector unit within a detector window, defined by the helix, by means of a reconstruction unit, the connecting lines from the radiation source to the two edges of the detector window, being mutually offset in the direction of the axis of rotation,
    intersecting two segments of the helix which are offset by a distance $(2n+1)p$ in the direction of the axis of rotation, where n is a small integer number larger than or equal to 1 and p corresponds to an axial offset between two neighboring turns of the helix, so that the Radon domain is regionally filled with a different degree of redundancy by the measuring data,
    and a cardiac motion signal representing the cardiac motion is detected by means of a cardiac motion signal detection device, and that on the basis of the cardiac motion signal such measuring data is selected from among the measuring data regionally redundantly filling the Radon domain such that the Radon domain is completely and homogeneously filled with measuring data from cardiac motion phases with as little motion as possible.

* * * * *